US011937807B2

(12) United States Patent
Munday

(10) Patent No.: US 11,937,807 B2
(45) Date of Patent: Mar. 26, 2024

(54) APPARATUS FOR CLOSING A SURGICAL SITE

(71) Applicant: George Swope Munday, Danville, KY (US)

(72) Inventor: George Swope Munday, Danville, KY (US)

(*) Notice: Subject to any disclaimer, the term of this patent is extended or adjusted under 35 U.S.C. 154(b) by 0 days.

(21) Appl. No.: 18/305,818

(22) Filed: Apr. 24, 2023

(65) Prior Publication Data

US 2023/0255622 A1 Aug. 17, 2023

Related U.S. Application Data

(62) Division of application No. 17/341,497, filed on Jun. 8, 2021, now abandoned.

(51) Int. Cl.
*A61B 17/06* (2006.01)
*A61B 34/30* (2016.01)
(Continued)

(52) U.S. Cl.
CPC ........ *A61B 17/06133* (2013.01); *A61B 34/30* (2016.02); *A61B 2017/06142* (2013.01)

(58) Field of Classification Search
CPC ... A61B 34/37; A61B 34/30; A61B 2090/037; A61B 2034/742; A61B 2034/302; A61B 2017/06142; A61B 17/06133; A61B 17/06114; A61B 17/06166; A61B 2017/00663; A61B 2017/0477; A61B 2017/06157; B65D 85/24
USPC .......... 128/887, 898; 206/63, 204, 210, 216, 206/219, 225, 227, 338, 339, 345, 350, 206/363, 364, 365, 366, 370, 380, 382, 206/383, 388, 394, 408, 438, 460, 476, 206/480, 523, 526, 562, 570, 572, 738, 206/766, 818, 822, 45.23, 63.3, 63.5; 220/254, 254.6; 221/1, 25, 46, 72, 129,
(Continued)

(56) References Cited

U.S. PATENT DOCUMENTS 633,404 A 9/1899 Warburton
3,901,244 A 8/1975 Schweizer
(Continued)

FOREIGN PATENT DOCUMENTS

CN 206482618 U 9/2017
CN 107811664 A 3/2018
(Continued)

OTHER PUBLICATIONS

PCT Search Report and Written Opinion completed by the ISA/US and issued in connection with PCT/US2018/045517.
(Continued)

*Primary Examiner* — Anthony D Stashick
*Assistant Examiner* — Marcos Javier Rodriguez Molina
(74) *Attorney, Agent, or Firm* — Barnes & Thornburg LLP

(57) ABSTRACT

A suturing device includes a clamshell body having a first side coupled to a second side by a hinge at a hinge end. The first side and the second side each have a cantilevered end opposite the hinge end. The clamshell body is configured to actuate between an open position and a closed position. A suture retainer is positioned within the clamshell body and is configured to receive a suture. An opening is formed in a wall of the second side of the clamshell body.

20 Claims, 8 Drawing Sheets

(51) Int. Cl.
  *A61B 34/00* (2016.01)
  *A61B 34/37* (2016.01)
  *A61B 90/00* (2016.01)

(58) Field of Classification Search
  USPC ..... 221/305; 224/222; 227/9, 175, 176, 177,
    227/178, 179, 180, 19, 175.1, 175.3,
    227/176.1, 177.1, 178.1, 179.1, 180.1;
    600/37, 102, 104, 106, 107, 109, 111,
    600/112, 114, 117, 118, 127, 129, 130,
    600/139, 141, 142, 146, 153, 160, 164,
    600/166, 170, 171, 173, 175, 178, 182,
    600/201, 204, 205, 206, 210, 214, 215,
    600/407, 417, 424, 427, 439, 476, 567,
    600/595; 604/22, 27, 43, 48, 57, 87, 93,
    604/264, 284, 93.01, 385.02; 606/1, 34,
    606/37, 41, 49, 68, 74, 79, 92, 94, 104,
    606/108, 119, 130, 139, 142, 143, 144,
    606/145, 146, 147, 148, 151, 153, 155,
    606/157, 167, 170, 174, 185, 191, 200,
    606/205, 206, 208, 209, 213, 215, 216,
    606/219, 222, 223, 224, 228, 232, 264,
    606/279, 305, 323, 326, 327, 914, 86 A;
    163/1, 5; D24/145
  See application file for complete search history.

(56) References Cited

U.S. PATENT DOCUMENTS

| | | | |
|---|---|---|---|
| 4,089,409 A * | 5/1978 | Cerwin | A61B 17/06138 606/228 |
| 4,126,221 A * | 11/1978 | Cerwin | A61B 17/06138 606/228 |
| 4,582,196 A * | 4/1986 | Hughson | D05C 1/065 206/83 |
| D301,373 S | 5/1989 | Peters | |
| 4,967,902 A | 11/1990 | Sobel et al. | |
| 5,021,059 A | 6/1991 | Kensey et al. | |
| 5,059,201 A | 10/1991 | Asnis | |
| 5,089,012 A | 2/1992 | Prou | |
| 5,099,994 A | 3/1992 | Kalinski et al. | |
| 5,160,339 A | 11/1992 | Chen et al. | |
| 5,171,253 A | 12/1992 | Klieman | |
| 5,179,818 A * | 1/1993 | Kalinski | A61B 17/06133 53/409 |
| 5,325,868 A | 7/1994 | Kimmelstiel | |
| 5,413,585 A | 5/1995 | Pagedas | |
| 5,507,775 A | 4/1996 | Ger et al. | |
| 5,514,159 A | 5/1996 | Matula et al. | |
| 5,675,961 A | 10/1997 | Cerwin et al. | |
| 5,683,402 A | 11/1997 | Cosgrove et al. | |
| 5,735,877 A | 4/1998 | Pagedas | |
| 5,830,157 A | 11/1998 | Foote | |
| 5,911,728 A | 6/1999 | Sepetka et al. | |
| 5,944,739 A | 8/1999 | Zlock et al. | |
| 6,015,428 A | 1/2000 | Pagedas | |
| 6,050,981 A | 4/2000 | Lampropoulos et al. | |
| 6,066,160 A | 5/2000 | Colvin et al. | |
| 6,126,677 A | 10/2000 | Ganaja et al. | |
| 6,135,272 A * | 10/2000 | Sobel | A61B 17/06133 206/380 |
| 6,138,440 A * | 10/2000 | Gemma | A61B 17/06133 53/430 |
| 6,143,004 A | 11/2000 | Davis et al. | |
| 6,200,329 B1 | 3/2001 | Fung et al. | |
| 6,214,332 B1 | 4/2001 | Askill et al. | |
| 6,293,961 B2 | 9/2001 | Schwartz et al. | |
| 6,471,715 B1 | 10/2002 | Weiss | |
| 6,860,895 B1 | 3/2005 | Akerfeldt et al. | |
| 6,939,357 B2 | 9/2005 | Navarro et al. | |
| 7,033,379 B2 | 4/2006 | Peterson | |
| 7,144,412 B2 | 12/2006 | Wolf et al. | |
| 7,204,841 B2 | 4/2007 | Green | |
| 7,322,161 B2 * | 1/2008 | Prescott | A61B 17/06166 242/129 |
| 7,351,249 B2 | 4/2008 | Hnojewyj et al. | |
| 7,407,505 B2 | 8/2008 | Sauer et al. | |
| 7,468,068 B2 | 12/2008 | Kolster | |
| 7,470,256 B2 | 12/2008 | Lampropoulos et al. | |
| 7,520,869 B2 | 4/2009 | Lampropoulos et al. | |
| 7,544,187 B2 | 6/2009 | Lampropoulos et al. | |
| 7,547,296 B2 | 6/2009 | Lampropoulos et al. | |
| 7,582,105 B2 | 9/2009 | Kolster | |
| 8,459,446 B2 * | 6/2013 | Kozlowski | A61B 17/06133 53/430 |
| D744,648 S * | 12/2015 | Wentling | D24/145 |
| 9,220,489 B2 | 12/2015 | Tegels | |
| 9,326,765 B2 | 5/2016 | Lane et al. | |
| 9,370,368 B2 | 6/2016 | Jayant | |
| 9,468,435 B2 | 10/2016 | Ashland | |
| 9,636,105 B2 | 5/2017 | Bagaoisan et al. | |
| 9,655,622 B2 | 5/2017 | Jonn et al. | |
| 9,775,601 B2 | 10/2017 | Keating et al. | |
| 10,660,635 B2 | 5/2020 | Munday | |
| 11,751,986 B2 * | 9/2023 | Bunch | A61F 2/0095 206/438 |
| 2003/0204195 A1 | 10/2003 | Keane et al. | |
| 2004/0133239 A1 | 7/2004 | Singhatat | |
| 2004/0260344 A1 | 12/2004 | Lyons et al. | |
| 2005/0033365 A1 | 2/2005 | Courage | |
| 2005/0085855 A1 | 4/2005 | Forsberg | |
| 2006/0058844 A1 | 3/2006 | White et al. | |
| 2006/0069397 A1 | 3/2006 | Nobles et al. | |
| 2006/0106418 A1 | 5/2006 | Seibold et al. | |
| 2006/0106423 A1 | 5/2006 | Weisel et al. | |
| 2006/0265006 A1 | 11/2006 | White et al. | |
| 2007/0004991 A1 | 1/2007 | Shelton | |
| 2007/0032821 A1 | 2/2007 | Chin-Chen et al. | |
| 2007/0210131 A1 | 9/2007 | Yarborough et al. | |
| 2008/0015635 A1 | 1/2008 | Olsen et al. | |
| 2008/0015636 A1 | 1/2008 | Olsen et al. | |
| 2008/0097479 A1 | 4/2008 | Boehlke et al. | |
| 2008/0269785 A1 | 10/2008 | Lampropoulos et al. | |
| 2008/0300629 A1 | 12/2008 | Surti | |
| 2009/0043246 A1 | 2/2009 | Dominguez | |
| 2009/0069847 A1 | 3/2009 | Hashiba et al. | |
| 2009/0076546 A1 | 3/2009 | Ashley et al. | |
| 2009/0143817 A1 | 6/2009 | Akerfeldt | |
| 2009/0234295 A1 | 9/2009 | Lampropoulos et al. | |
| 2009/0275980 A1 | 11/2009 | Zeiner et al. | |
| 2010/0230300 A1 | 9/2010 | Hunter et al. | |
| 2011/0215005 A1 * | 9/2011 | Cerwin | A61B 17/06133 206/63.3 |
| 2012/0010634 A1 | 1/2012 | Crabb et al. | |
| 2013/0165954 A1 | 6/2013 | Dreyfuss et al. | |
| 2013/0310856 A1 | 11/2013 | Sherts et al. | |
| 2015/0038991 A1 | 2/2015 | Prior et al. | |
| 2015/0088195 A1 | 3/2015 | Moustafa | |
| 2015/0157316 A1 | 6/2015 | Labarbera | |
| 2016/0376240 A1 | 12/2016 | Bunnelle et al. | |
| 2017/0112487 A1 | 4/2017 | Martin et al. | |
| 2017/0196555 A1 * | 7/2017 | Kirsch | B65D 25/108 |
| 2017/0245843 A1 | 8/2017 | Kim | |
| 2017/0245852 A1 | 8/2017 | Kim | |
| 2018/0206842 A1 * | 7/2018 | Wentling | A61B 17/06123 |
| 2019/0350580 A1 * | 11/2019 | Munday | A61B 17/0482 |

FOREIGN PATENT DOCUMENTS

| | | | |
|---|---|---|---|
| EP | 0460784 A1 | 12/1991 | |
| EP | 494081 B1 | 1/1992 | |
| EP | 0494081 A1 | 7/1992 | |
| EP | 0608138 A2 | 7/1994 | |
| EP | 0623310 A2 * | 11/1994 | A61B 17/06138 |
| EP | 608138 A3 | 3/1995 | |
| EP | 884023 A1 * | 12/1998 | A61B 17/06133 |
| EP | 1997437 A2 * | 12/2008 | A61B 17/06133 |
| JP | 2013-534170 A | 9/2013 | |
| JP | 2015-231572 A | 12/2015 | |
| KR | 101736309 B1 | 5/2017 | |

(56) References Cited

FOREIGN PATENT DOCUMENTS

| WO | 9826719 A1 | 6/1998 | | |
|---|---|---|---|---|
| WO | 0051498 A1 | 9/2000 | | |
| WO | 2006050080 A2 | 5/2006 | | |
| WO | 2008033766 A2 | 3/2008 | | |
| WO | 2008150773 A1 | 12/2008 | | |
| WO | 2009052509 A1 | 4/2009 | | |
| WO | 2009114811 A2 | 9/2009 | | |
| WO | WO-2015138966 A1 * | 9/2015 | ......... | A61B 17/0483 |
| WO | 2016014579 A1 | 1/2016 | | |
| WO | WO-2016014579 A1 * | 1/2016 | ....... | A61B 17/06123 |
| WO | 2017180092 A1 | 10/2017 | | |

OTHER PUBLICATIONS

Japanese Office Action for Application No. 2021-514281, dated May 12, 2022, 4 pages.
European Office Action for Application No. 18806708.6, dated Jan. 10, 2022, 6 pages.
Extended European Search Report for Application No. 22162407.5, dated Aug. 29, 2022, 85 pages.

* cited by examiner

APPARATUS FOR CLOSING A SURGICAL SITE

CROSS-REFERENCE TO RELATED APPLICATIONS

This application is a divisional patent application of U.S. patent application Ser. No. 17/341,497, filed Jun. 8, 2021, which is herein incorporated by reference in its entirety.

TECHNICAL FIELD

The present disclosure relates to surgical instruments and particularly, to an instrument and method to enhance suture management within robotic surgical cases.

BACKGROUND

The use of robotic technology within the operating room has been increasing at an astounding rate. In 2017, there were approximately 644,000 robotic assisted surgical cases performed in the United States alone. Robotic assisted surgery is utilized globally in multiple surgical subspecialties. These include: cardiac surgery, thoracic surgery, gynecology, urology, otolaryngology, colorectal surgery, and general surgery. Within each of these specialties there are a variety of robotic cases in which suture is required.

Suture management within a robotic case is a common barrier to efficient surgical workflow. Poor suture management results in: increased operative times; knotting, fracturing, or accidental cutting of the suture; frustration for the surgeon; and ultimately a barrier to more frequent use of the robotic technology. Currently, surgeons navigate this suture management issue by substituting a long suture length with multiple shorter suture length to complete a case. This methodology generates increased total volume and expense of suture; increased OR expenses via longer operative times; and increased potential for a retained needle within the patient.

The disclosed embodiments will aid in efficient suture management in robotic surgery. It will decrease overall cost and increase patient safety across all robotic surgical specialties. Ultimately this device and method will assist with the global proliferation of computer-aided surgery.

SUMMARY

The present disclosure includes one or more of the features recited in the appended claims and/or the following features which, alone or in any combination, may comprise patentable subject matter.

According to a first aspect of the disclosed embodiments, a suturing device includes a clamshell body configured to be inserted into a surgical site of a patient. The clamshell body has a first side coupled to a second side by a hinge at a hinge end. The first side and the second side each have a cantilevered end opposite the hinge end. The clamshell body is configured to actuate between an open position and a closed position. A suture retainer is positioned within the clamshell body and configured to receive a suture. An opening is formed in a wall of the second side of the clamshell body. An end of the suture is configured to extend through the opening when the clamshell body is in the closed position so that the suture is accessible within the surgical site of the patient.

In some embodiments of the first aspect, a cartridge may be configured to be removably positioned in the suture retainer. The suture may be configured to be wound around the cartridge and moved from around the cartridge to around the suture retainer. The suture retainer may extend from an inner wall of the first side of the clamshell body. The suture retainer may include at least one peg. The suture may be configured to be positioned around the at least one peg. The suture may be configured to be positioned on the suture retainer by a caregiver during a medical procedure for the patient.

Optionally, in the first aspect, at least one notch may be formed in at least one of the first side and the second side of the clamshell. A surgical robotic arm may be configured to couple to the clamshell body at the at least one notch. The at least one notch may be formed adjacent the hinge end. A first notch may be formed in the hinge end of the first side of the clamshell body. A second notch may be formed in the hinge end of the second side of the clamshell body.

It may be contemplated, in the first aspect, that the opening is formed in the cantilevered end of the second side of the clamshell body. A latch may be provided on the cantilevered end of the second side of the clamshell body. The latch may be configured to secure the first side of the clamshell body to the second side of the clamshell body when the clamshell body is in the closed position.

According to a second aspect of the disclosed embodiments, a suturing device includes a clamshell body configured to be inserted into a surgical site of a patient. The clamshell body has a first side coupled to a second side by a hinge at a hinge end. The first side and the second side each have a cantilevered end opposite the hinge end. The clamshell body is configured to actuate between an open position and a closed position. A plurality of pegs extends from an inner wall of the first side of the clamshell body and is configured to receive a suture. An opening is formed in a wall of the second side of the clamshell body. An end of the suture is configured to extend through the opening when the clamshell body is in the closed position so that the suture is accessible within the surgical site of the patient.

In some embodiments of the second aspect, a cartridge may be configured to be removably positioned between the plurality of pegs. The suture may be configured to be wound around the cartridge and moved from around the cartridge to around the plurality of pegs. The plurality of pegs may include two rows of pegs. The suture may be configured to be positioned around the plurality of pegs. The suture may be configured to be positioned around the plurality of pegs by a caregiver during a medical procedure for the patient.

Optionally, in the second aspect, at least one notch may be formed in at least one of the first side and the second side of the clamshell. A surgical robotic arm may be configured to couple to the clamshell body at the at least one notch. The at least one notch may be formed adjacent the hinge end. A first notch may be formed in the hinge end of the first side of the clamshell body. A second notch may be formed in the hinge end of the second side of the clamshell body.

It may be desired, in the second aspect, that the opening is formed in the cantilevered end of the second side of the clamshell body. A latch may be provided on the cantilevered end of the second side of the clamshell body. The latch may be configured to secure the first side of the clamshell body to the second side of the clamshell body when the clamshell body is in the closed position.

BRIEF DESCRIPTION OF THE DRAWINGS

The detailed description particularly refers to the accompanying figures in which.

DETAILED DESCRIPTION

Figure 1:
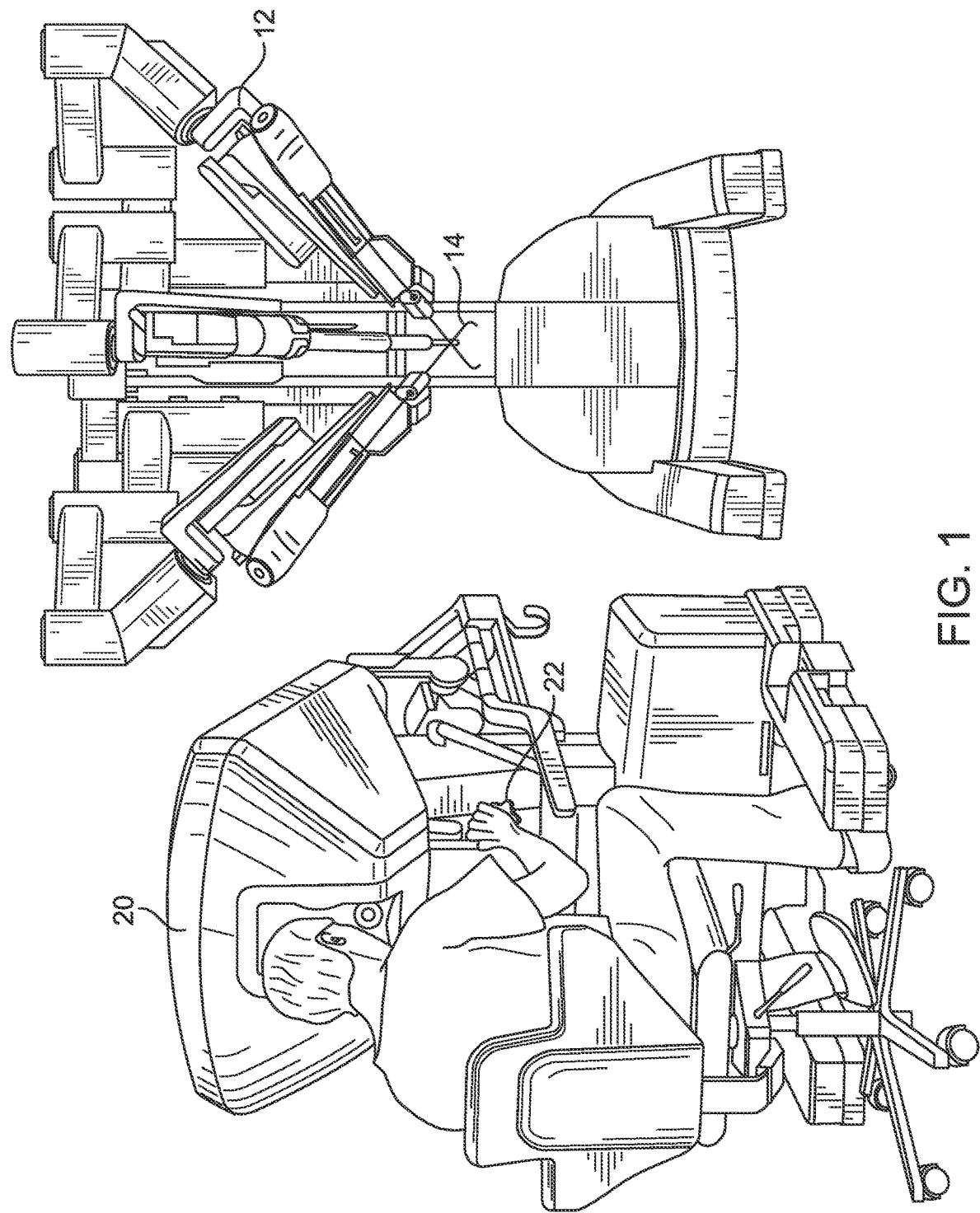
FIG. 1 is a perspective view of an automated surgical system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an automated surgery system 10 includes at least one robotic arm 12 having a plurality of fingers 14 to grab surgical instruments. The robotic arm 12 is positioned at a surgical site so that the robotic arm 12 can manipulate the instruments at the surgical site. A control panel 20 includes a plurality of controls 22, e.g. a joystick, for a surgeon to manipulate the robotic arms 12 during surgery.

Figure 2:
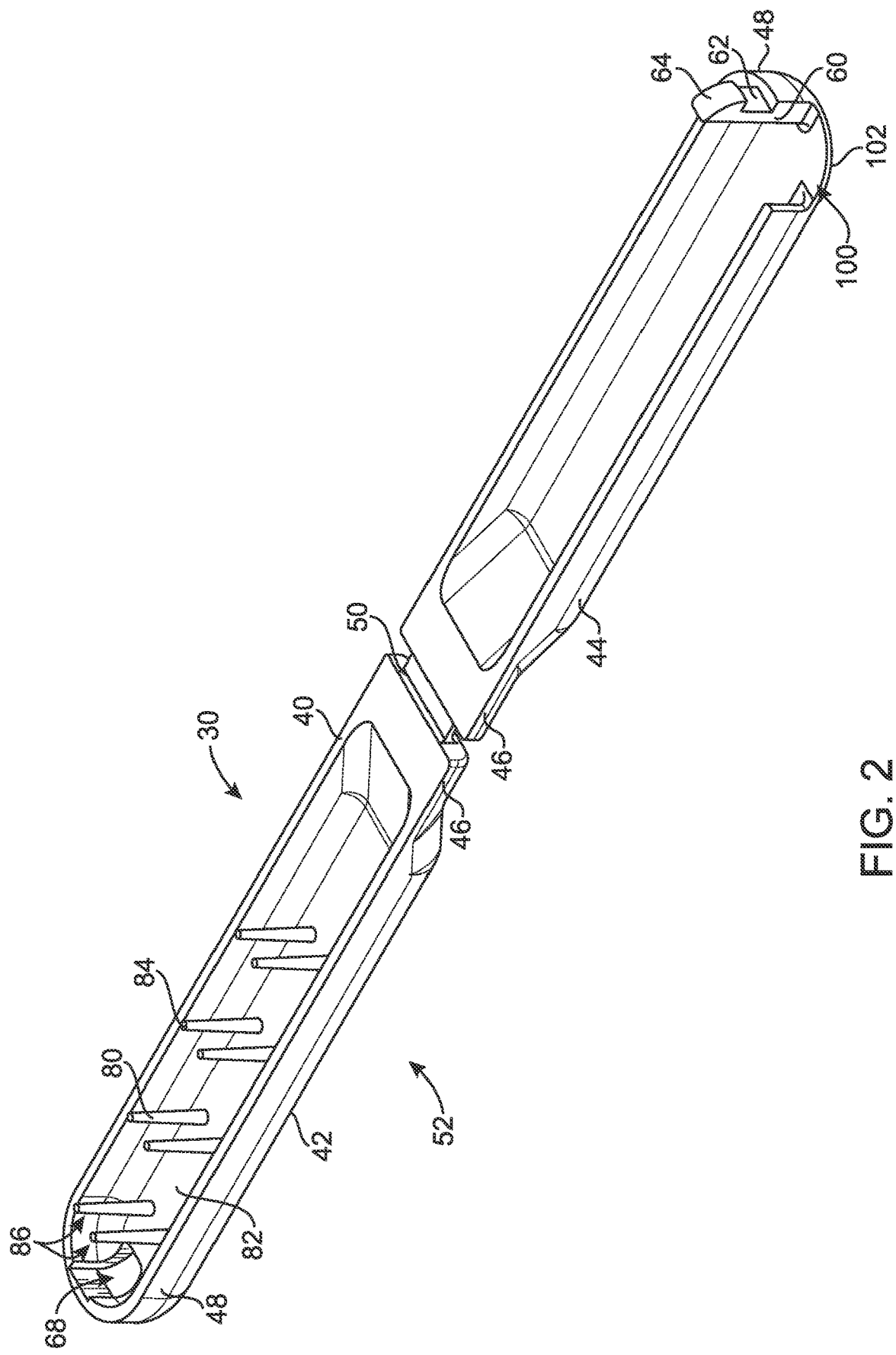
FIG. 2 is a top perspective view of a suturing device having a clamshell body including a first side coupled to a second side by a hinge at a hinge end, wherein the clamshell body is in an open position.

Referring to FIG. 2, a suturing device 30 is configured for use with the system 10 by securing the suturing device 30 to one of the plurality of fingers 14 of the robotic arm 12. The suturing device 30 is configured to be inserted into a surgical site of a patient to facilitate closing the surgical site after a surgical procedure. The suturing device 30 retains a suture 32 (described in more detail below) that can be pulled from the suturing device 30 to facilitate closing the surgical site. The suture 32 is configured to be pulled from the suturing device 30 while the suturing device 30 is inserted in the surgical site, e.g. inside the patient. The suture 32 is threaded through tissue that is to be closed before the suturing device 30 is removed from the surgical site. After the suturing device 30 is removed from the surgical site the suture 32 is tied together in at least one location to close the surgical site. In at least one embodiment, the suture 32 is wound within the suturing device 30 by a caregiver or technician prior to the surgical procedure. Accordingly, the suturing device 30 can accommodate any suture type used within a healthcare facility. A caregiver or technician selects the appropriate suture type for the surgical procedure, and the appropriate suture type is wound within the suturing device 30 at the healthcare facility prior to the surgical procedure. In another embodiment, the suturing device 30 may be pre-loaded with the suture 32.

Figure 4:
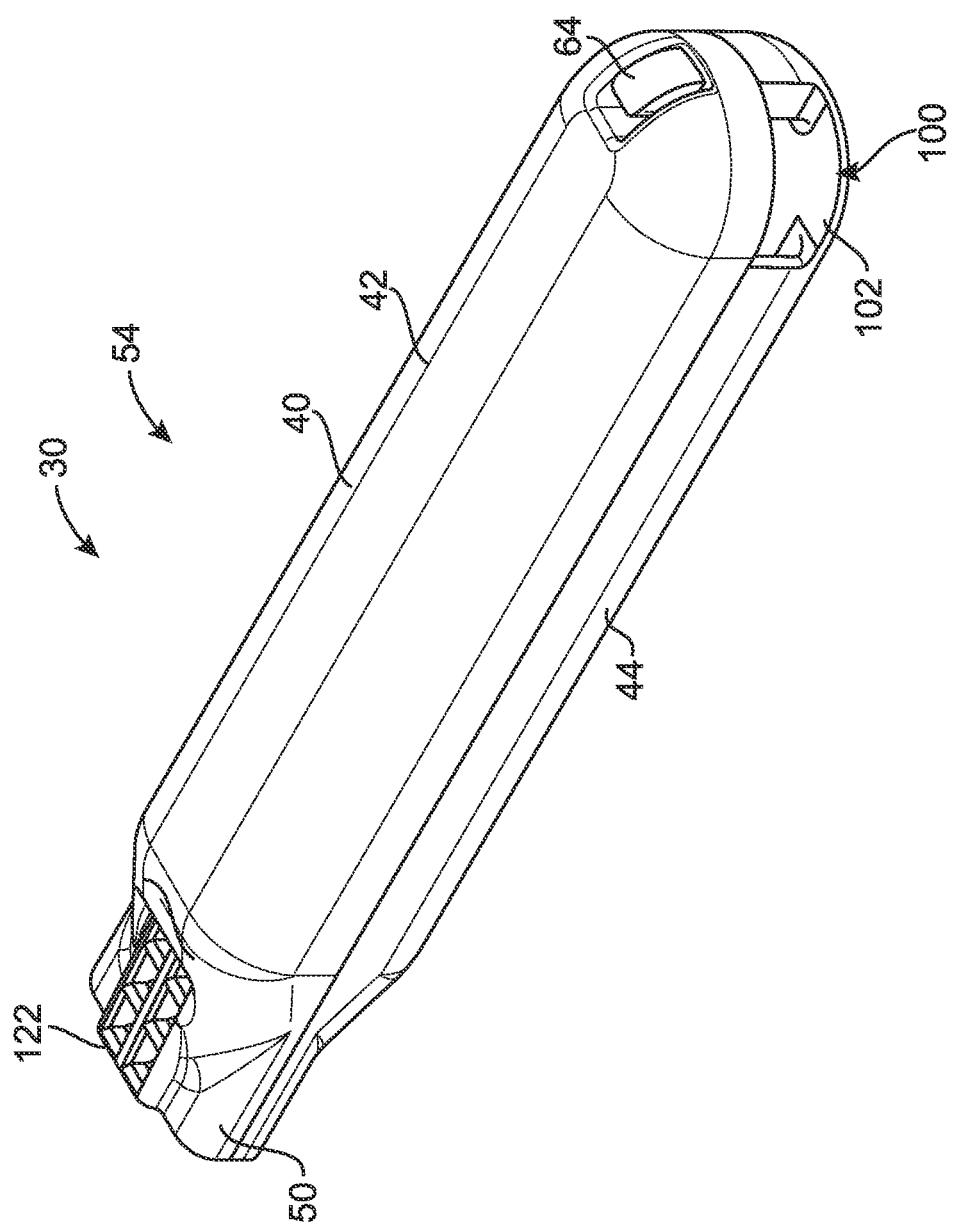
FIG. 4 is a top perspective view of the clamshell body in a closed position.

The suturing device 30 includes a clamshell body 40 having a first side 42 and a second side 44. Each of the first side 42 and the second side 44 includes a hinge end 46 and a cantilevered end 48. A pair of sidewalls 56 extend between the hinge end 46 and the cantilevered end 48 of each of the first side 42 and the second side 44. The first side 42 is coupled to the second side 44 by a hinge 50 at the hinge end 46 of the first side 42 and the second side 44. The hinge 50 enables the clamshell body 40 to articulate between an open position 52 (shown in FIG. 2) and a closed position 54 (shown in FIG. 4). The cantilevered end 48 of the second side 44 of the clamshell body 40 includes latch 60 having an arm 62 and an outwardly extending flange 64 extending from an end 66 of the arm 62. The cantilevered end 48 of the first side 42 of the clamshell body 40 includes an opening 68. The latch 60 is configured to extend though the opening 68 so that the flange 64 secures the first side 42 of the clamshell body 40 to the second side 44 of the clamshell body 40 when the clamshell body 40 is in the closed position 54 (as shown in FIG. 4).

Referring to FIG. 2, a suture retainer 80 is positioned within the clamshell body 40 and configured to receive the suture 32. The suture retainer 80 extends from an inner wall 82 of the first side 42 of the clamshell body 40. The suture retainer 80 includes a plurality of pegs 84 extending from the inner wall 82. In the illustrative embodiment, the plurality of pegs 84 are arranged in two rows 86 extending between the hinge end 46 and the cantilevered end 48 of the first side 42 of the clamshell body 40. In other embodiments, the suturing device 30 may include only one row 86 of pegs 84 or more than two rows 86 of pegs 84. In may be contemplated that the suturing device 30 only includes one peg 84 in some embodiments. In some embodiments, the caregiver or technician winds the suture 32 around the suture retainer 80 at the healthcare facility. In other embodiments, the suture is pre-loaded around the suture retainer 80.

An opening 100 is formed in the cantilevered end 48 of the second side 44 of the clamshell body 40. In the illustrative embodiment, the opening 100 is formed in a corner 102 of the cantilevered end 48 of the second side 44 of the clamshell body 40. In other embodiments, the opening 100 may be centered in the cantilevered end 48 of the second side 44 of the clamshell body 40. In yet another embodiment, the opening 100 may be formed in the sidewall 56 of the second side 44. It may also be contemplated that the opening 100 is formed in a sidewall 56 of the first side 42, in some embodiments. When the suture 32 is wound around the suture retainer 80, and end 110 of the suture 32 having a needle 112 extends from the suturing device 30 (as described in more detail below).

Figure 3:
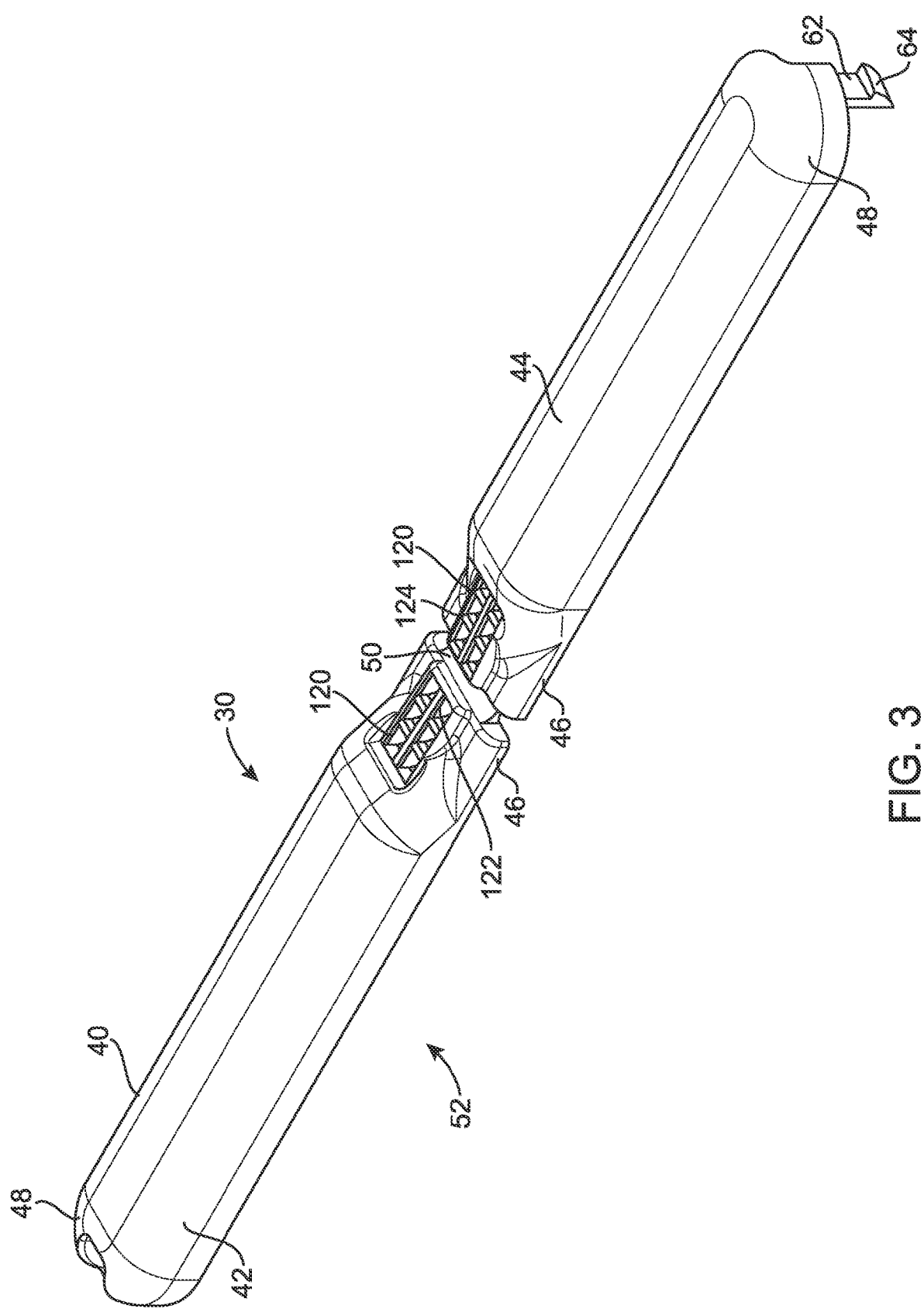
FIG. 3 is a bottom perspective view of the clamshell body in the open position.

Referring now to FIG. 3, notches 120 are formed adjacent the hinge end 46 of each of the first side 42 and the second side 44 of the suturing device 30. In particular, a first set of notches 122 are formed adjacent the hinge end 46 of the first side 42, and a second set of notches 124 are formed adjacent the hinge end 46 of the second side 44. In the closed position 54 (as shown in FIG. 4), the first set of notches 122 are positioned opposite the second set of notches 124. The fingers 14 of the robotic arm 12 are configured to grip the suturing device 30 at the notches 120 so that the suturing device 30 is secured to the system 10 during the surgical procedure.

Figure 5:
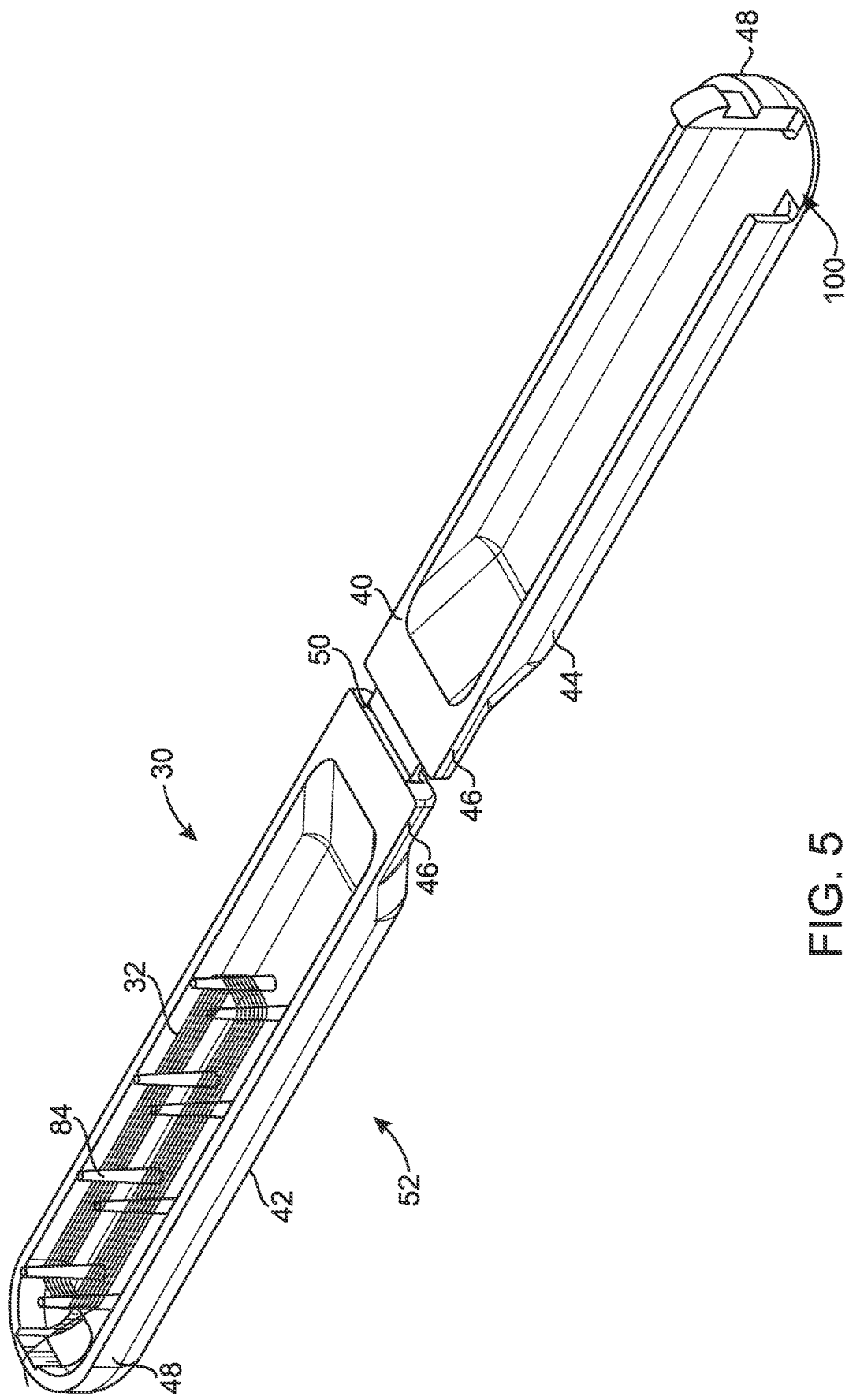
FIG. 5 is a top perspective view of the clamshell body in the open position and having a suture would around a suture retainer.
Figure 6:
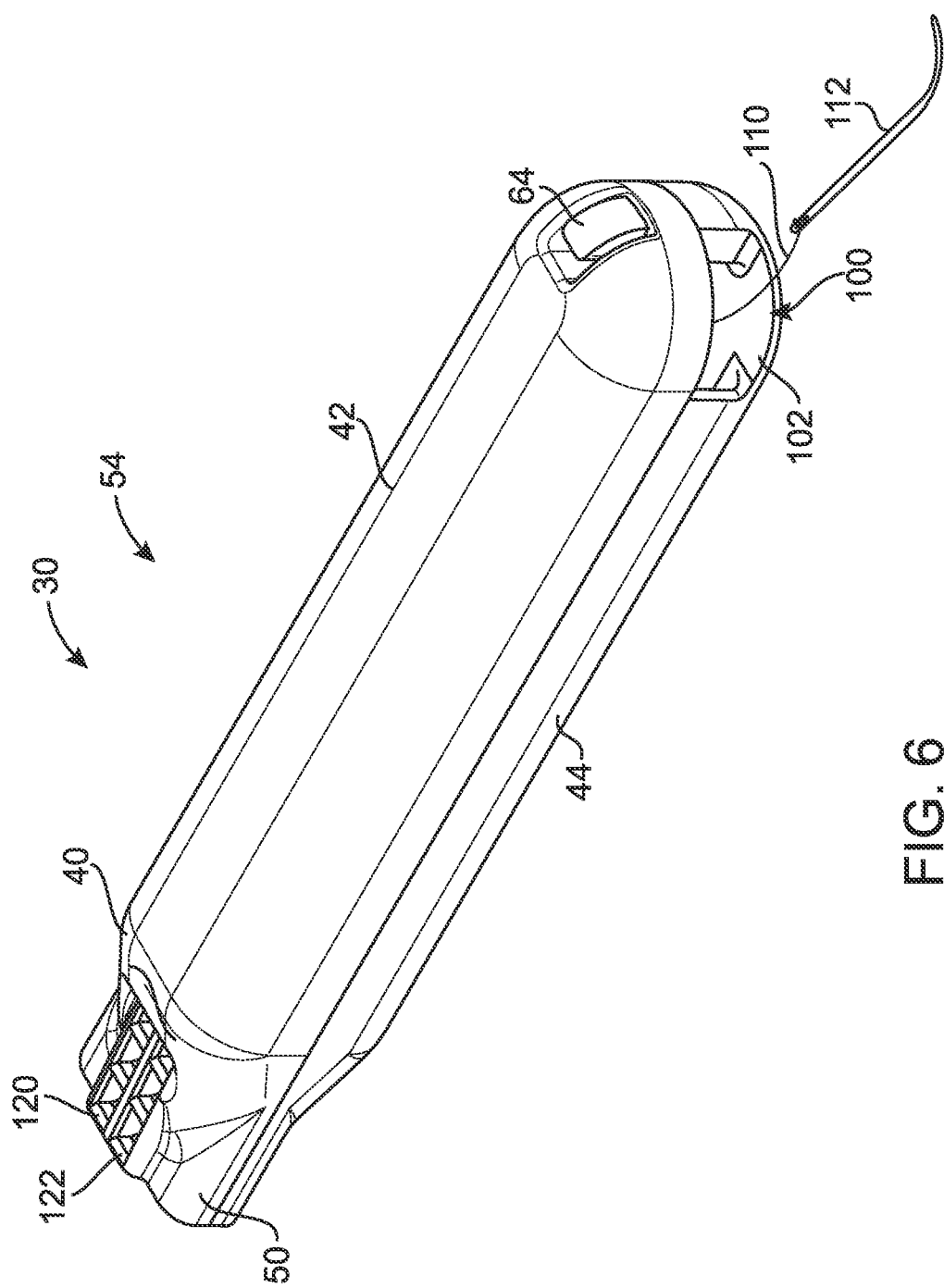
FIG. 6 is a top perspective view of the clamshell body in the closed position and having an end of the suture extending through an opening.

FIG. 5 illustrates the suture 32 wound around the suture retainer 80. The suture 32 is would around the outside of the suture retainer 80 in loops. That is, the suture 32 is wound around the outside of each of the plurality of pegs 84. As illustrated in FIG. 6, in the closed position 54, the end 110 of the suture 32 extends through the opening 100. Accordingly, the needle 112 can be pulled by the fingers 14 of the robotic arm 12 to unwind the suture 32 and pull the suture 32 through the opening 100 during the surgical procedure. By unwinding the suture 32, the suture may be passed through the patient's tissue to facilitate closing the surgical site.

Figure 7:
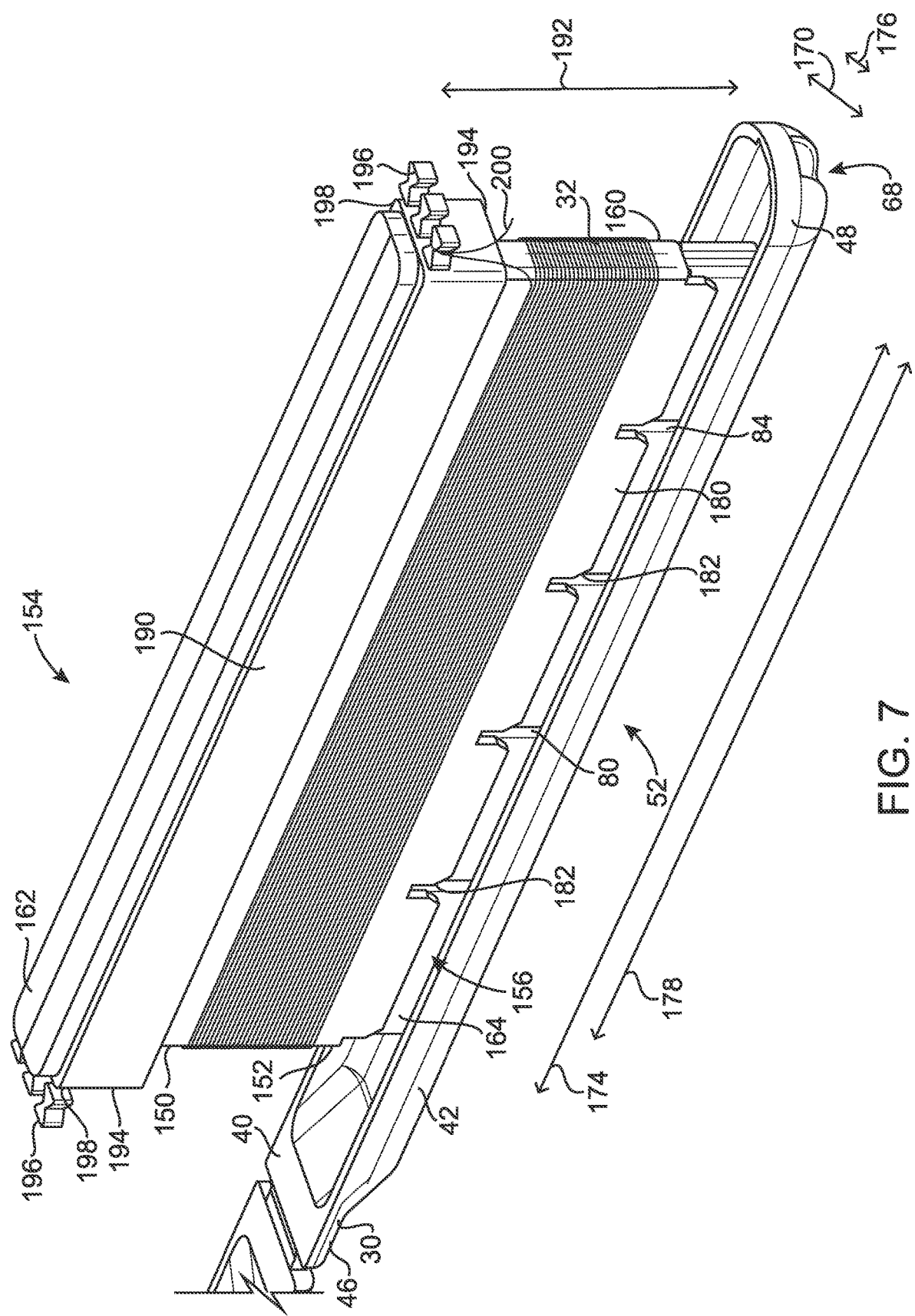
FIG. 7 is a perspective view of an embodiment of a cartridge configured to receive the suture.

Referring now to FIG. 7, a cartridge 150 for positioning the suture 32 in the device 30 includes a body 152. The body 152 includes a top end 154 and a bottom end 156. A main body 160 extends from a flange 162 at the top end 154 to a lower body 164 at the bottom end 156. The main body 160 has a width 170 and a length 174 that is larger than a width 176 and a length 178 of the lower body 164 so that a ledge 180 is formed between the main body 160 and the lower body 164. A plurality of notches 182 are formed at the ledge 180 and extend into the main body 160.

A sliding bracket 190 extends around the main body 160. The bracket 190 is configured to slide along a height 192 of the main body 160. The bracket 190 is prevented from sliding off the top end 154 of the cartridge 150 by the flange 162. The bracket 190 includes opposite ends 194 that each have a plurality of suture tabs 196 attached thereto. The suture tabs 196 each include a break point 198 that enables the tab 196 to be detached from the bracket 190.

During the surgical procedure, the suture 32 is wound around the main body 160 by a caregiver. In some embodiments, the suture 32 is pre-loaded around the main body 160 prior to the surgical procedure. An end 200 of the suture 32 positioned opposite the end 110 of the suture 32 is secured to one of the suture tabs 196. In some embodiments, the suture 32 may be utilized without the suture tab 196.

The lower body 164 of the cartridge 150 is removably positioned in the suture retainer 80. In the illustrative embodiment, the lower body 164 is positioned between the pegs 84. Each peg 84 extends into one of the notches 182 in the main body 160 to secure the cartridge 150 into the device 30. With the cartridge 150 positioned in the device 30, the bracket 190 is slid down the main body 160 to push the suture 32 off of the main body 160 and around the suture retainer 80, e.g. around the pegs 84.

With the suture 32 secured around the suture retainer 80, the suture tab 196 to which the end 200 of the suture 32 is secured is broken off of the bracket 190 at the break point 198. In some embodiments, the suture tab 196 is broken off the bracket 190 prior to sliding the suture 32 onto the suture retainer 80. The cartridge 150 is then removed from the device 30 and the device 30 is moved to the closed position, shown in FIG. 6, with the end 110 of the suture 32 extending through the opening 100. The device is inserted into the surgical site of the patient and the suture 32 is pulled from the device 30 to stitch the surgical site. When all of the suture 32 is removed from the device 30, the suture tab 196 anchors against the tissue of the patient inside the surgical site to secure the suture 32.

Figure 8:
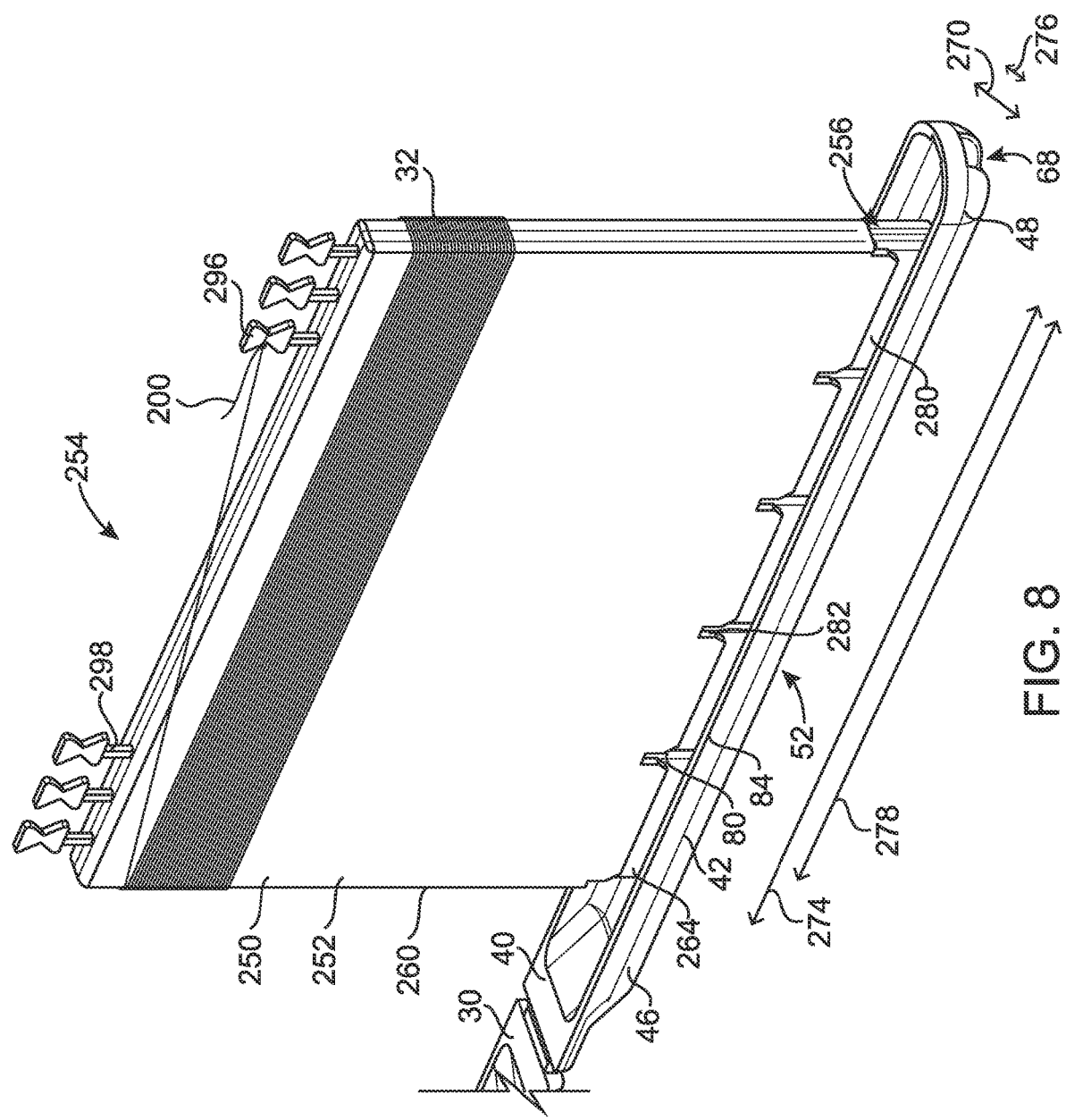
FIG. 8 is a perspective view of another embodiment of a cartridge configured to receive the suture.

Referring now to FIG. 8, another cartridge 250 for positioning the suture 32 in the device 30 includes a body 252. The body 252 includes a top end 254 and a bottom end 256. A main body 260 extends from the top end 254 to a lower body 264 at the bottom end 256. The main body 260 has a width 270 and a length 274 that is larger than a width 276 and a length 278 of the lower body 264 so that a ledge 280 is formed between the main body 260 and the lower body 264. A plurality of notches 282 are formed at the ledge 280 and extend into the main body 260. The main body 260 includes a plurality of suture tabs 296 extending from the top end 254. The suture tabs 296 each include a break point 298 that enables the tab 296 to be detached from the main body 260. In some embodiments, the cartridge 250 may also include a sliding bracket similar to sliding bracket 190.

During the surgical procedure, the suture 32 is wound around the main body 260 by a caregiver. In some embodiments, the suture 32 is pre-loaded around the main body 260 prior to the surgical procedure. The end 200 of the suture 32 is secured to one of the suture tabs 296. In some embodiments, the suture 32 may be utilized without the suture tab 296.

The lower body 264 of the cartridge 250 is removably positioned in the suture retainer 80. In the illustrative embodiment, the lower body 264 is positioned between the pegs 84. Each peg 84 extends into one of the notches 282 in the main body 260 to secure the cartridge 250 into the device 30. With the cartridge 250 positioned in the device 30, a caregiver slides the suture 32 down the main body 260 to push the suture 32 off of the main body 260 and around the suture retainer 80, e.g. around the pegs 84. In some embodiments, a sliding bracket similar to sliding bracket 190 is used to move the suture 32 onto the suture retainer 80.

With the suture 32 secured around the suture retainer 80, the suture tab 296 to which the end 200 of the suture 32 is secured is broken off of the bracket 290 at the break point 298. In some embodiments, the suture tab 296 is broken off prior to moving the suture 32 onto the suture retainer 80. The cartridge 250 is then removed from the device 30 and the device 30 is moved to the closed position, shown in FIG. 6, with the end 110 of the suture 32 extending through the opening 100. The device is inserted into the surgical site of the patient and the suture 32 is pulled from the device 30 to stitch the surgical site. When all of the suture 32 is removed from the device 30, the suture tab 296 anchors against the tissue of the patient inside the surgical site to secure the suture 32.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles can have been presented, they need not be utilized in combination, and many combinations of aspects and principles are possible in light of the various embodiments provided above.

The invention claimed is:

1. A suturing device comprising:
    a clamshell body configured to be inserted into a surgical site of a patient, the clamshell body having a first side coupled to a second side by a hinge at a hinge end, the first side and the second side each having a cantilevered end opposite the hinge end, wherein the clamshell body is configured to actuate between an open position and a closed position;
    a suture retainer positioned within the clamshell body and configured to receive a suture;
    an opening formed in a wall of the second side of the clamshell body, wherein an end of the suture is configured to extend through the opening when the clamshell body is in the closed position so that the suture is accessible within the surgical site of the patient; and
    a cartridge configured to be removably positioned in the suture retainer, wherein the cartridge is configured to enable the suture to be wound around the suture retainer, wherein the suture is wound around the cartridge before positioning the cartridge in the suture retainer, and wherein, after positioning the cartridge in the suture retainer with the suture attached, the suture is moved from around the cartridge to around the suture retainer.

2. The suturing device of claim 1, wherein the suture retainer extends from an inner wall of the first side of the clamshell body.

3. The suturing device of claim 1, wherein the suture retainer includes at least one peg, wherein the suture is configured to be positioned at least partially on the at least one peg.

4. The suturing device of claim 1, wherein the suture is configured to be positioned on the suture retainer by a caregiver during a medical procedure for the patient.

5. The suturing device of claim 1, further comprising at least one notch formed in at least one of the first side and the second side of the clamshell body, wherein a surgical robotic arm is configured to couple to the clamshell body at the at least one notch.

6. The suturing device of claim 5, wherein the at least one notch is formed adjacent the hinge end.

7. The suturing device of claim 5, further comprising:
    a first notch formed in the hinge end of the first side of the clamshell body; and
    a second notch formed in the hinge end of the second side of the clamshell body.

8. The suturing device of claim 1, wherein the opening is formed in the cantilevered end of the second side of the clamshell body.

9. The suturing device of claim 1, further comprising a latch on the cantilevered end of the second side of the clamshell body, wherein the latch is configured to secure the first side of the clamshell body to the second side of the clamshell body when the clamshell body is in the closed position.

10. A suturing device comprising:
    a clamshell body configured to be inserted into a surgical site of a patient, the clamshell body having a first side coupled to a second side by a hinge at a hinge end, the first side and the second side each having a cantilevered end opposite the hinge end, wherein the clamshell body is configured to actuate between an open position and a closed position;
    a plurality of pegs extending from an inner wall of the first side of the clamshell body and configured to receive a suture;
    an opening formed in a wall of the second side of the clamshell body, wherein an end of the suture is configured to extend through the opening when the clamshell body is in the closed position so that the suture is accessible within the surgical site of the patient; and
    a cartridge configured to be removably positioned between the plurality of pegs, wherein the cartridge is configured to enable the suture to be wound around the plurality of pegs, wherein the cartridge includes a plurality of cartridge notches, wherein each of the plurality of pegs is received in one of the plurality of cartridge notches when the cartridge is positioned between the plurality of pegs.

11. The suturing device of claim 10, wherein the suture is configured to be wound around the cartridge and moved from around the cartridge to around the plurality of pegs.

12. The suturing device of claim 10, wherein the plurality of pegs includes two rows of pegs.

13. The suturing device of claim 10, wherein the suture is configured to be positioned around the plurality of pegs.

14. The suturing device of claim 10, wherein the suture is configured to be positioned around the plurality of pegs by a caregiver during a medical procedure for the patient.

15. The suturing device of claim 10, further comprising at least one clamshell notch formed in at least one of the first side and the second side of the clamshell body, wherein a surgical robotic arm is configured to couple to the clamshell body at the at least one clamshell notch.

16. The suturing device of claim 15, wherein the at least one clamshell notch is formed adjacent the hinge end.

17. The suturing device of claim 15, further comprising:
    a first clamshell notch formed in the hinge end of the first side of the clamshell body; and
    a second clamshell notch formed in the hinge end of the second side of the clamshell body.

18. The suturing device of claim 10, wherein the opening is formed in the cantilevered end of the second side of the clamshell body.

19. The suturing device of claim 10, further comprising a latch on the cantilevered end of the second side of the clamshell body, wherein the latch is configured to secure the first side of the clamshell body to the second side of the clamshell body when the clamshell body is in the closed position.

20. The suturing device of claim 1, further comprising a bracket that slides along the cartridge to assist in moving the suture from the cartridge to the suture retainer.

* * * * *